United States Patent [19]

Chrisey et al.

[11] Patent Number: 5,688,642

[45] Date of Patent: Nov. 18, 1997

[54] SELECTIVE ATTACHMENT OF NUCLEIC ACID MOLECULES TO PATTERNED SELF-ASSEMBLED SURFACES

[75] Inventors: Linda A. Chrisey, Bowie; Walter J. Dressick, Ft. Washington, both of Md.; Jeffrey M. Calvert, Alexandria, Va.

[73] Assignee: The United States of America as represented by the Secretary of the Navy, Washington, D.C.

[21] Appl. No.: 352,126

[22] Filed: Dec. 1, 1994

[51] Int. Cl.$^6$ .................... C12Q 1/68; C12Q 1/70; C12P 19/34; C07H 21/04
[52] U.S. Cl. .................... 435/6; 435/5; 435/91.1; 435/91.2; 435/176; 204/403; 536/24.3; 536/24.33; 536/24.32; 536/25.3; 356/445
[58] Field of Search .................... 435/6, 5, 91.1, 435/91.2, 176; 204/403; 356/445; 536/24.3, 24.33, 25.3

[56] References Cited

U.S. PATENT DOCUMENTS

| | | | |
|---|---|---|---|
| 4,562,157 | 12/1985 | Lowe et al. | |
| 5,077,085 | 12/1991 | Schnur et al. | 427/98 |
| 5,077,210 | 12/1991 | Eigler | 435/176 |
| 5,079,600 | 1/1992 | Schnur et al. | 357/4 |
| 5,200,051 | 4/1993 | Cozzette et al. | 204/403 |
| 5,252,743 | 10/1993 | Barrett et al. | 548/303.7 |
| 5,391,463 | 2/1995 | Ligler et al. | |
| 5,482,830 | 1/1996 | Bogart et al. | 435/5 |

FOREIGN PATENT DOCUMENTS

WO 94/27719  12/1994  WIPO ............ B01J 19/00

OTHER PUBLICATIONS

Chrisey et al., Mat. Res. Soc. Symp. Proc. vol. 330, pp. 179–184 (1994).
Fodor et al., Science, vol. 251, pp. 767–773 (1991).
Bhatia et al., Anal. Bioch., 208, pp. 001–012 (1993).
Kawai et al., Anal. Bioch., 209, pp. 63–69 (1993).
Seiki et al., Proc. Natl. Acad. Sci. USA, vol. 86, pp. 6230–6234 (1989).
Calvert, Jeff M., J. Voac. Sci. Technol. B 11(6), Nov./Dec. 1993, pp. 2155–2163.
Calvert, Jeff M., "Lithographically Patterned Self-Assembled Films", Thin Films, vol. 20: Organic Thin Films and Surfaces, A. Ulman, Ed., Academic Press, Boston (1995), 109–141. (Invited Paper).

Primary Examiner—W. Gary Jones
Assistant Examiner—Dianne Rees
Attorney, Agent, or Firm—Thomas E. McDonnell; Barry A. Edelberg

[57] ABSTRACT

Patterns of pre-formed hybridizable nucleic acid oligomers are formed upon a substrate. The substrate is coated with molecules, such as aminosilanes, whose reactivity with nucleic acid molecules can be transformed by irradiation. The coated substrate exposed to patterned irradiation then contacted with pre-formed nucleic acid oligomers. The binding of the preformed nucleic acid oligomers to the coating molecules may be covalent or non-covalent (for example, ionic bonding or hydrogen bonding). If desired, a heterobifunctional crosslinker may be employed, before or after irradiation, with the coating to promote covalent binding of the nucleic acid oligomers to the coating molecules. Also, the irradiation step may be performed with the assistance of a positive-tone or negative-tone photoresist.

18 Claims, 5 Drawing Sheets

SELECTIVE ATTACHMENT OF NUCLEIC ACID MOLECULES TO PATTERNED SELF-ASSEMBLED SURFACES

BACKGROUND OF THE INVENTION

1. Field of the Invention

The present invention relates generally to the attachment of nucleic acids to substrates and more particularly to the formation of a pattern of nucleic acid molecules attached to a substrate.

2. Description of the Background Art

Biomolecules, preferably nucleic acids, have been immobilized on a variety of solid surfaces, for a number of known applications, including DNA and RNA oligomer synthesis; separation of desired target nucleic acids from mixtures of nucleic acids including RNA; conducting sequence-specific hybridizations to detect desired genetic targets (DNA or RNA); creating affinity columns for mRNA isolation; quantification and purification of PCR reactions; characterization of nucleic acids by AFM and STM; and for sequence determination of unknown DNAs, such as the human genome. A number of methods have been employed to attach nucleic acids to solid surfaces, but there is an increasing need to immobilize multiple nucleic acids of unique or distinct sequences and which retain their specific functions in a high resolution, spatially controlled fashion on rugged, solid substrates.

The above applications have used a variety of substrates for DNA immobilization, including polymeric membranes (nylon, nitrocellulose), magnetic particles, mica, glass or silica, gold, cellulose, and polystyrene.

Methods which have been employed for the attachment of preformed synthetic or naturally occurring nucleic acids to solid surfaces for the above mentioned applications and on the aforementioned substrates have included: electrodeposition, UV crosslinking, (nitrocellulose, nylon); electrostatic, covalent linking, and exploitation of strong intermolecular ligand/receptor binding as for enzyme- or protein-linked affinity methods.

Certain methods, such as the UV-crosslinking and some covalent attachment methods, are considered non-specific, that is the reactive group on the nucleic acid involved in attachment to the surface cannot be well controlled, such as crosslinking of nucleic acids to aminosilane films using glutaraldehyde (for binding DNA to optical fibers) and UV-crosslinking methods for attachment to nylon or nitrocellulose membranes.

While many of these attachment modalities may be appropriate for the attachment of a single nucleic acid species to the desired surface, most are inadequate for the attachment of multiple species, especially at the high resolutions required for applications involving very large numbers of DNA species. For example, biotin-labeled DNA molecules of different sequences could be separated as a collective group from a milieu of other molecules using streptavidin-functionalized magnetic particles, but this technique cannot resolve the individual DNA molecules of different sequences, as would be required for applications involving multiple hybridization events such as the simultaneous detection of many genetic targets.

UV crosslinking of multiple nucleic acid species to a single filter can be achieved, but at low resolution, as separation of molecules of different sequence is accomplished by placement of liquid portions of nucleic acids at the desired position on the filter. This method is limited in the number of reactions that could be accomplished on a given surface area, which is a limitation for automation of applications on a micrometer scale.

Non-specific covalent linking methods, such as the reaction of glutaraldehyde with amines, are inadequate because the glutaraldehyde can react with different moieties on the nucleic acid, may form polymeric materials, and diminish the number of functional nucleic acid molecules on the surface. Prior art covalent attachment methods meet the criterion of specific directed immobilization of DNA through a selected chemical moiety on the DNA to a specific moiety on the surface, but do not address the issue of pattern or array formation using spatial control of the immobilization process.

Before the present invention, no attempts were made to define spatially resolved regions in which nucleic acids are selectively bound from regions to which nucleic acids are excluded, other than by placement of liquid aliquots (generally >1 µl) of nucleic acids to the desired position on the filter, wafer, etc. To date, other efforts to spatially separate individual nucleic acid species have focused on the use of polystyrene, 96-well microtiter plates or minidisks of glass for the purposes of sequence analysis or hybridization reactions. The method whereby an epoxysilane was used to modify a $SiO_2$ surface, and subsequently reacted with aminoterminated DNA oligomers was useful for immobilization of multiple, unique DNA species, but required the use of a fluid microjet apparatus to deliver small volume aliquots to the surface. This approach to spatially resolving discrete nucleic acid species on the surface results in problems with cross-contamination between closely adjacent areas which are meant to contain distinct molecules, and also has an inherent limit to smallest feature size achievable, dependent upon the fluid delivery system employed. Additionally, the fluid microjet apparatus is expensive.

Methods have been described in the literature for the spatially controlled modification of surfaces with peptides and proteins, and also for synthetic nucleic acids. For example, DNA oligomers have been synthesized, at the substrate surface, in a stepwise fashion (i.e., one nucleic acid base at a time) using photochemical activation of photosensitive protecting groups on the DNA base monomers followed by condensation of subsequent nucleic acid bases, capping and oxidation of the phosphorous from P(III) to P(V). The specific conditions of the surface modification chemistry and solid substrate utilized were not described. The DNA oligomers are arranged in small-scale arrays using initial photolithographic modification of the substrate through a mask. This approach is quite limited in its ability to fabricate arrays containing distinctly different or unrelated DNA molecules. Such arrays are best prepared using standard solid phase DNA oligomer synthesis and purification techniques on a large scale, followed by immobilization of the pre-formed DNA molecules in defined patterns on the surface. This method also does not permit the immobilization of DNA species other than synthetic molecules, such as isolated sequences of naturally-derived DNA. The third drawback to this previous method is that each individual with its component DNA array must be fabricated individually, that is, the attachment of the final DNA sequence requires sequential irradiation and condensation steps for each oligomer set, adding numerous additional steps. For example, synthesis of a 20 base DNA oligomer (a 20-mer) by this previous method requires eighty steps, twenty photolysis steps and twenty nucleic acid condensations, twenty oxidations of the phosphorous group and twenty cappings of any unwanted hydroxy groups. This number of steps can seriously compromise the quality and homogeneity of the final oligomer product. If each step of the forty steps proceeds in 99% yield—an optimistic value—the overall yield of correctly synthesized oligomers is only 67%. For a 95% average yield per step, the overall yield of correctly synthesized oligomers would drop to 13%. Clearly, the likelihood of using prior art methods to correctly synthesize a usefully large number of identical nucleic acid oligomers upon a single surface is small if not nil. This problem also bears on the difficulties that the prior art has faced in immobilizing hybridizable nucleic acid oligomers. The ability to hybridize requires a minimum length of nucleic acid. Yet, with each nucleic acid condensation step, the prior art methods provide a significantly reduced yield of correctly synthesized nucleic acid oligomer and increased potential for the generation of nonhybridizable failure sequences.

SUMMARY OF THE INVENTION

It is an object of the present invention to covalently or non-covalently immobilize a controlled density of functional nucleic acid molecules (hereinafter abbreviated as NAMs), particularly nucleic acid oligomers, on a substrate under conditions that maintain the specific function of the molecule.

It is another object of the present invention to provide a method for preparing surfaces which contain at least one co-planar patterned area to which NAMs may be immobilized, as well as at least one area resistant to the covalent or non-covalent attachment of NAMs, resulting in the formation of arrays or patterns of NAMs.

It is a further object of the present invention to sequentially immobilize distinct NAMs in a well-defined pattern on the surface of a substrate.

It is yet another object of the present invention to provide sensors or biomaterials for a variety of biological, analytical, electronic or optical materials uses.

These and other objects have been achieved by the present method for forming a pattern of nucleic acid molecules, particularly nucleic acid oligomers, on a surface. A layer of molecules bearing reactive functional groups, such as organosilane reagents, are covalently bound to the surface of a substrate. If desired, the layer may be further modified with a heterobifunctional crosslinker that attaches to a reactive functional group of the covalently bound molecule at one active site and includes a second active site available for attachment to a NAM or modified NAM. The covalently bound molecules and any heterobifunctional cross-linker are selected so that the ability of the surface to bind NAMs is modified by exposure of that surface to suitable radiation (e.g., electrons, ions, x-rays and glow discharge or other plasma), typically u.v. radiation. After the surface is irradiated in a selected pattern, the surface is exposed to the NAM to be attached. The NAM can be derived from synthetic (man-made from nucleic acid monomers) or naturally occurring sources.

The process may be repeated, permitting the attachment of a plurality of NAMs, each in a distinct pattern.

BRIEF DESCRIPTION OF THE DRAWINGS

A more complete appreciation of the invention will be readily obtained by reference to the following Description of the Preferred Embodiments and the accompanying drawings in which like numerals in different figures represent the same structures or elements, wherein.

DETAILED DESCRIPTION OF THE PREFERRED EMBODIMENT(S)

Initially, an organosilane coating is covalently attached to the hydroxylated surface of a substrate having exposed hydroxyl groups, such as silicon dioxide, to form an organosilane film or coating. This film or coating is typically a monolayer or a bilayer. The organosilane is selected to have at least one reactive site that covalently binds to the hydroxylated surface of the substrate and another reactive site that is incapable of binding either to other organosilane molecules of the coating or to the substrate.

Thus, the organosilane molecules of the coating have a bound reactive site and a free reactive site. This free reactive site remains available for binding to a molecule distinct from both the substrate and other organosilane molecules in the coating.

Figure 1:
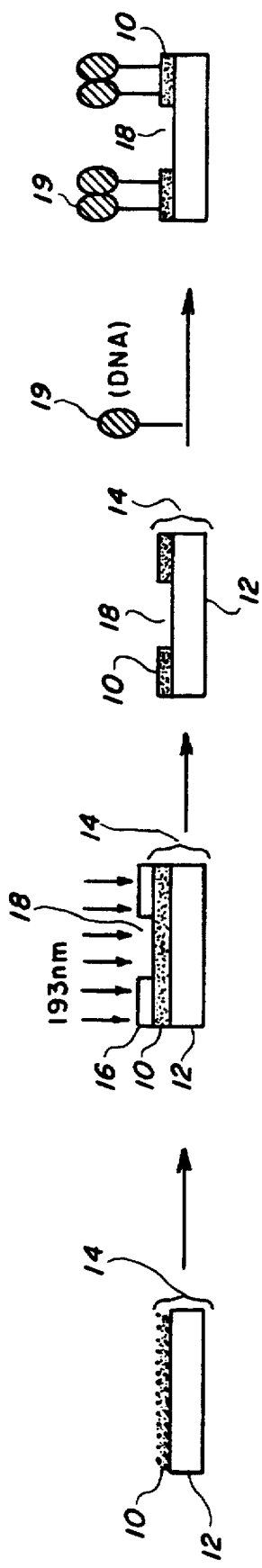
FIG. 1 is a schematic flow chart for nucleic acid patterning according to one embodiment of the present invention.
Figure 2:
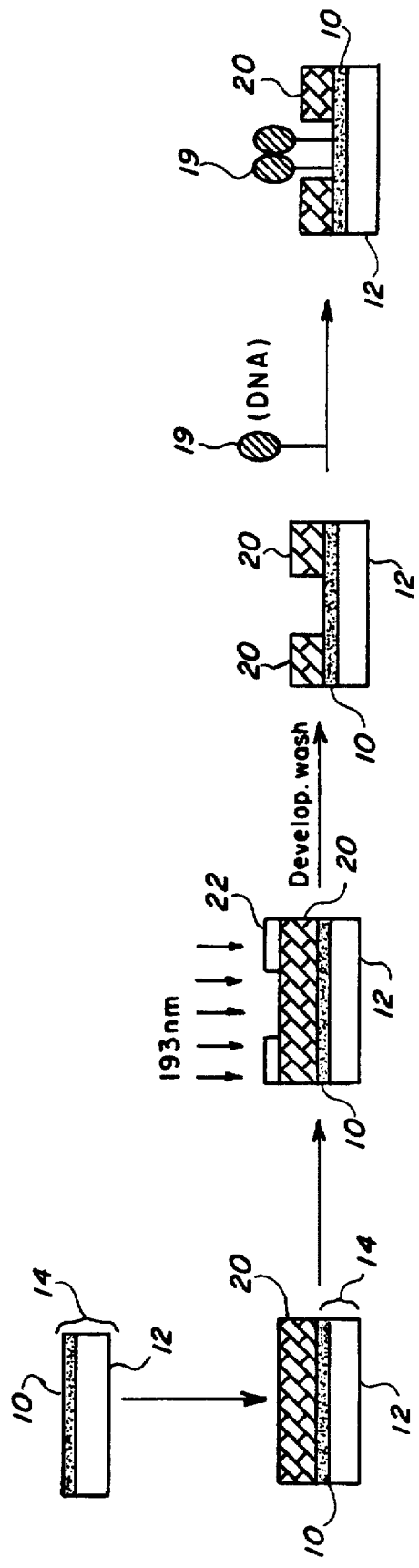
FIG. 2 is a schematic flow chart for nucleic acid patterning according to another embodiment of the present invention.
Figure 3:
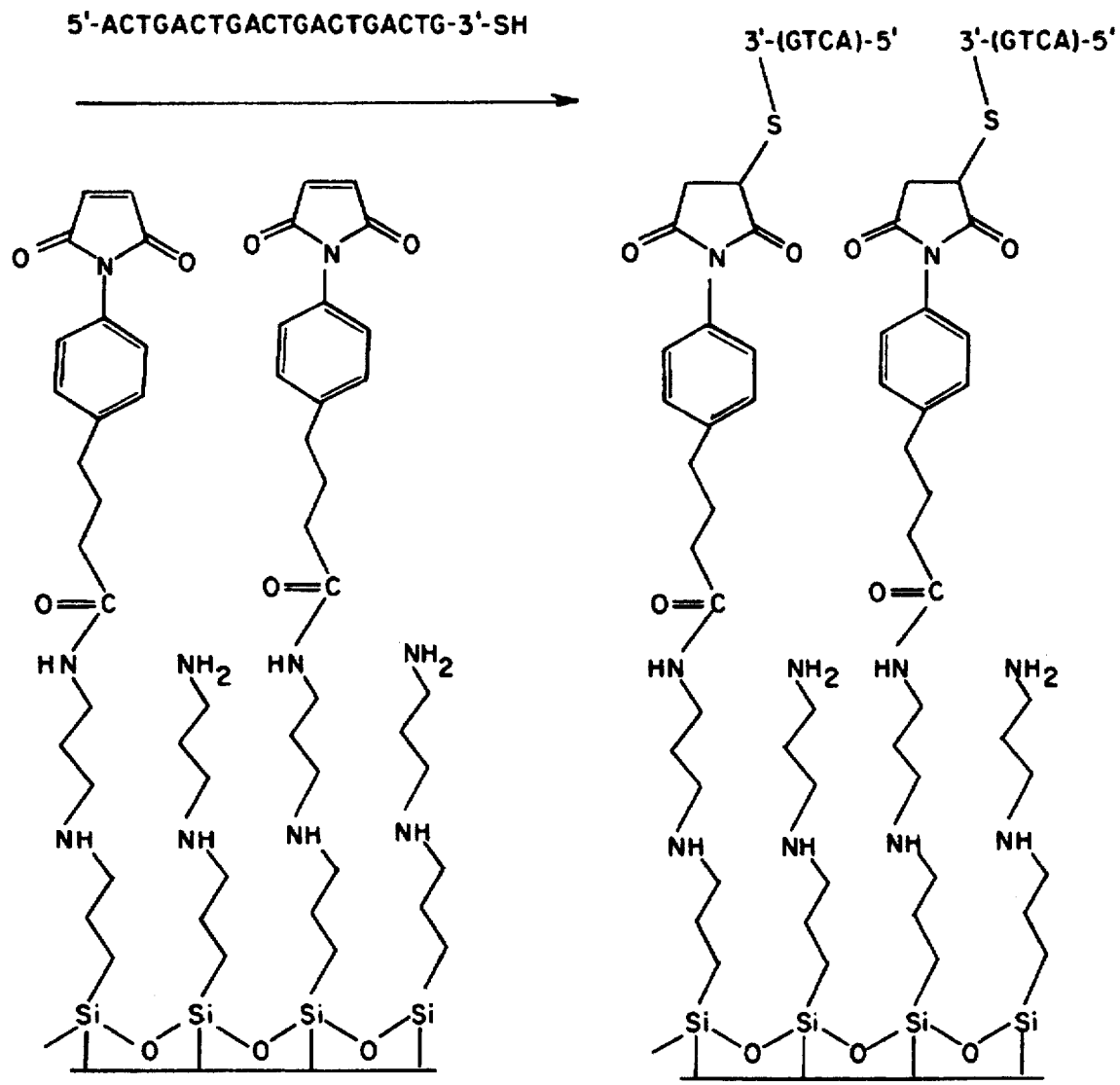
FIG. 3 shows the binding of a DNA oligomer to an EDA-modified silicon substrate.

Specifically, the free reactive site of the organosilane may directly bind to a modified or unmodified nucleic acid molecule (see FIG. 1 and FIG. 2) or may indirectly bind to a modified or unmodified nucleic acid molecule via a heterobifunctional crosslinker (see FIG. 1, FIG. 2 and FIG. 3). If the free reactive site of the organosilane is directly bound to a nucleic acid molecule, the binding is typically non-covalent (i.e., ionic bonding, or, less often, hydrogen bonding). Advantageously, non-covalent bonding of nucleic acid molecules generally disposes of any need to modify the desired nucleic acid molecules, as it typically may be performed using native nucleic acid molecules. On the other hand, non-covalently bound systems are expected to be less robust than covalently bound systems in the fabrication of arrays of oligomers of nucleic acids.

As shown in FIG. 1, an aminosilane coating 10 is applied over an SiO$_2$ substrate 12. The resulting structure 14 is irradiated with ultraviolet light (at 193 nm, for example) through a mask 16 positioned over aminosilane coating 10. The u.v. irradiation removes the portions of aminosilane coating 10 that were exposed through mask 16. Upon removal of mask 16, aminosilane coating 10 remains on those regions protected by the mask and are the native oxide of substrate 12 is exposed at any region 18 not protected by mask 16. A nucleic acid oligomer, shown here as oligomeric DNA 19, binds to the aminosilane coating 10, but not to the native oxide 18. This process forms a positive tone image in both the aminosilane film and also in the DNA.

FIG. 2 shows the use of a positive-tone photoresist in the method of the present invention. An aminosilane coating 10 is applied over an SiO$_2$ substrate 12. A positive-tone photoresist 20 is then applied over the entire surface of aminosilane coating 10. The resulting structure is irradiated with ultraviolet light through a mask 22 positioned over the photoresist. Development and washing removes the exposed portion of photoresist 20 and reveals underlying aminosilane film 10. Oligomeric DNA 19 binds to the exposed portions of aminosilane coating 10, but not to the remaining portions of photoresist 20. In the schemes of both FIG. 1 and FIG. 2, a surface having patterns of exposed amino functional groups is used for selective non-covalent attachment of DNA oligomers.

Any heterobifunctional crosslinker used should have a reactive site for bonding with the free reactive sites of the organosilane molecules and a free reactive site for directly bonding to the nucleic acid to be attached. For covalent bonding of oligomeric nucleic acid molecules to a substrate surface, the desired nucleic acid sequence is typically modified to contain a functional group that is reactive with the free reactive site of the selected heterobifunctional crosslinker (FIG. 3). Therefore, the patterned amine surfaces of FIGS. 1 and 2 may also be used for the covalent attachment of NAM oligomers.

The exposed surface of the substrate, whether it is a native organosilane coating or an organosilane coating that has been reacted with a heterobifunctional crosslinker, may then be overlaid with a layer of photoresist material. While the present invention can accommodate the use of either a negative tone or a positive tone photoresist, a positive tone photoresist is typically used. A positive- tone photoresist is one in which the areas exposed to irradiation become soluble in the developer, whereas areas which are protected from irradiation by opaque areas of the mask remain largely insoluble when treated with developer, i.e., the photoresist blocks access to the underlying crosslinker layer with its second reactive group. Conversely, a negative-tone photoresist is soluble only in the unexposed regions. For either type of photoresist, areas which remain coated with photoresist do not become coated with NAMs, either via non-covalent or covalent methods, i.e., these areas are largely resistant to NAM binding (FIG. 2).

In any event, the assembly containing the organosilane coating and any heterobifunctional crosslinker and/or photoresist is then irradiated, either in a defined pattern or through a mask which defines a pattern. The mask or irradiation pattern defines a pattern of areas exposed to the irradiation and areas unexposed to the irradiation on the substrate surface. Irradiation may be from numerous types of exposure sources, including light (infrared, visible, ultraviolet, x-ray), electron beams, ion beams and plasma.

Where no heterobifunctional crosslinker or photoresist is used before the irradiation step, the organosilane molecules (such as aminosilanes) in the irradiated portions of the organosilane coating are photolytically transformed to destroy the amine (nucleic acid binding) functional group and to produce a surface that is not a good surface for binding NAMs. The free reactive amine sites of the organosilane molecules in the unexposed portions of the organosilane coating remain available for the subsequent binding of NAMs, either directly or via heterobifunctional crosslinkers.

Where no heterobifunctional crosslinker is used before the irradiation step, but a positive-tone photoresist is employed, the photoresist coating at first renders the free reactive sites of the organosilane molecules unavailable for binding with NAMs. Upon irradiation, the exposed areas of the photoresist become soluble in the selected developer. Thus, these exposed areas of the photoresist are removed during development. The removal of the exposed areas of the positive photoresist renders the free reactive sites of the underlying organosilane molecules available for bonding to NAMs, either directly or via heterobifunctional crosslinkers. If a negative-tone photoresist were used, the unexposed regions would be soluble in and removable by the developer, while the regions exposed to irradiation would become insoluble in the developer and would remain after development.

The use of a heterobifunctional crosslinker simplifies the covalent attachment of NAMs. A heterobifunctional crosslinker has one first activated functional group reactive toward a specific chemical moiety on the exposed portion of the silane molecules, and a second activated functional group (which is not reactive toward either the first functional group of the crosslinker, nor with the free reactive group on the organosilane molecules) which will preferentially react with a specific chemical moiety on the NAM to effect a stable, covalent bond between the NAM and the hydroxylated surface.

A photoresist may also be applied over the layer of heterobifunctional crosslinker. If a positive tone photoresist is applied, the portions of the photoresist exposed to irradiation will become soluble in the selected developer and will thus be removed during development. The unexposed regions remain insoluble in the developer. Thus, the unexposed portions of the photoresist remain and prevent the covalent and non-covalent binding of NAM's to the second activated functional group of the heterobifunctional crosslinker. If a negative tone photoresist is used, the exposed portions of the photoresist are converted from a developer-soluble state to a developer insoluble state. In that scenario, only the unexposed portions of the photoresist will be removed during subsequent development.

Any heterobifunctional crosslinker used may be attached either before or after the substrate has been irradiated. If attached to the surface before irradiation, only regions of the surface in which the second activated functional group is exposed after development will bind NAMS. If attached to the surface after irradiation, the heterobifunctional crosslinker will attach only to those regions of the substrate surface where the organosilane molecules have exposed free reactive sites. Depending on the nature of the radiation-induced transformation, free reactive sites may be either created or destroyed in the exposed regions of the substrate.

Figure 4:
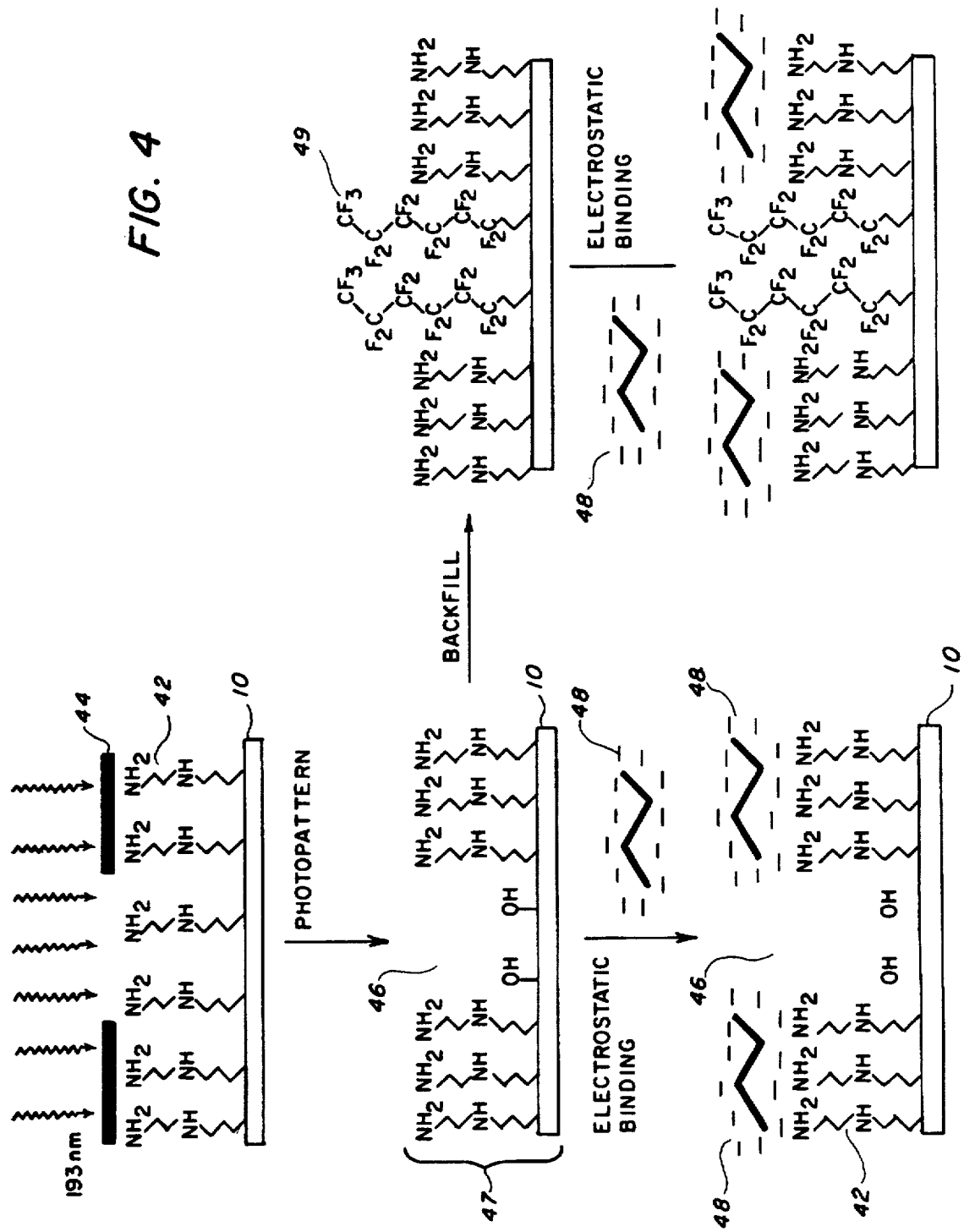
FIG. 4 is a schematic flow chart illustrating two alternative embodiments of the method of the present invention.

FIG. 4 further illustrates the method of the present invention. In FIG. 4, silica substrate 40 has an aminosilane coating 42 thereon, and is irradiated through mask 44. The portions 46 of aminosilane coating 42 exposed through mask 44 are removed by the irradiation, leaving a hydroxylated Si—OH surface. Resulting structure 47 may then be contacted with negatively charged DNA oligomer 48. The negatively charged DNA oligomer 48 electrostatically binds to the remaining portions of the aminosilane coating, but not to the exposed regions. Alternatively, resulting structure 47 can be backfilled with a second organosilane that is attached in the exposed regions of the surface. In the instance of FIG. 4, backfill is accomplished by attaching commercially available linear perfluorinated alkylsilane group 49 to portions 46. After backfilling, the resulting structure is contacted with negatively charged DNA oligomer 48. The negatively charged DNA oligomer 58 electrostatically binds to the remaining portions of the aminosilane coating, but not to the perfluoroalkyl groups.

Figure 5:
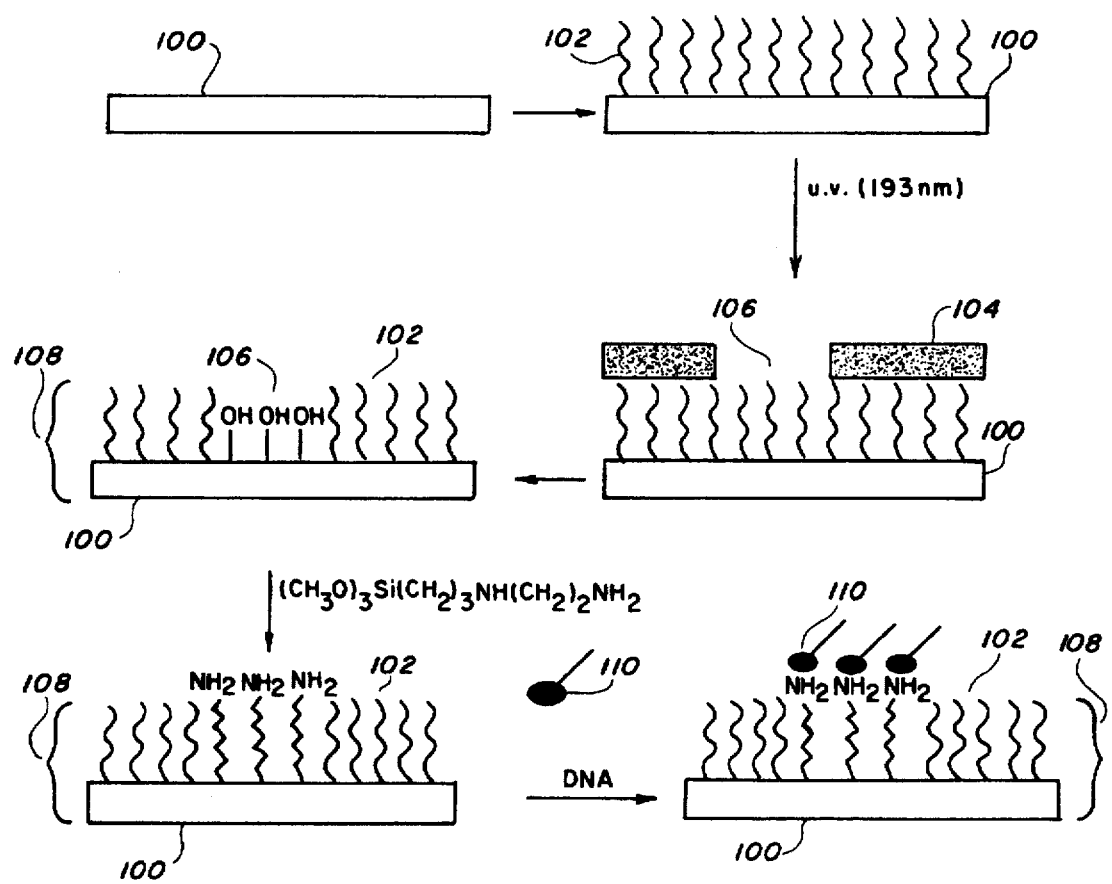
FIG. 5 is a schematic flow chart illustrating yet another method of nucleic acid patterning according to the present invention.

FIG. 5 shows yet another alternative embodiment according to the present invention. In FIG. 5, an $SiO_2$ substrate 100 is coated with a coating of a silane 102 that is resistant to the binding of nucleic acid oligomers. The resulting assembly is irradiated with ultraviolet light through patterned mask 104. The ultraviolet light selectively removes the non-DNA-binding silane from those regions 106 exposed thereto through mask 102, leaving a hydroxylated surface on $SiO_2$ substrate 100. When resulting structure 108 is contacted with a solution of, for example, an amino-terminated silane such as $(CH_3O)_3Si—(CH_2)_3NH(CH_2)_2NH_2$ (N-(2-aminoethyl)-3-aminopropyltrimethoxysilane, abbreviated as "EDA"), the silane functionality reacts with the free hydroxyl groups in regions 106. The amino terminus remains available for covalently binding NAMs, such as DNA oligomers 110. Alternatively, the amino terminus can be reacted with a heterobifunctional crosslinker that binds NAMs.

In conjunction with the method of the present invention, one may also employ known blocking agents to prevent non-specific binding and/or absorption of NAMs, proteins, enzymes, conjugates or small molecules used to detect the NAMs. Typical blocking agents include proteins, carbohydrates, detergents and amino acids.

The substrates to be modified for use in the method and product of the invention include materials which have or can be modified to have surface hydroxyl groups which can react with silanes. Suitable substrates are preferably inorganic materials, including but not limited to silicon, glass, silica, diamond, quartz, alumina, silicon nitride, platinum, gold, aluminum, tungsten, titanium, various other metals and various other ceramics. Alternatively, polymeric materials such as polyesters, polyamides, polyimides, acrylics, polyethers, polysulfones, fluoropolymers, etc. may be used as suitable organic substrates. The substrate used may provided in any suitable form, such as slides, wafers, fibers, beads, etc.

The nucleic acid-binding silanes useful for the invention can bind to the substrate's hydroxyl groups, and include a wide variety of silanes. Amino-terminated silanes are preferred for attachment of NAMs, although thiol-terminated silanes may also be employed, particularly in cases where the silane is to be reacted with a thiol-reactive group on a heterobifunctional crosslinker. Other silanes containing terminal functional groups such as olefins, acetals, epoxy and benzylhalides are also useful from crosslinker attachment. The hydroxyl-reactive terminus of the silane may be, for example, trichloro, trimethoxy, triethoxy, monoethoxy, chlorodimethyl or dimethylmethoxy. Typical silanes useful in the present invention include amino-terminated silanes such as EDA, trimethoxysilylpropyldiethylenetriamine (DETA), and (aminoethylaminomethyl)-phenylethyltrimethoxysilane (PEDA), aminopropyltriethoxysilane and aminobutyldimethylmethoxysilane.

Typically, the irradiation step is performed at a u.v. wavelength, although other wavelengths may be used, especially where differentiation between irradiated and non-irradiated regions of the surface is accomplished with the aid of a photoresist. U.V. radiation, when used, may be carried out using any number of UV sources, including pulsed ArF excimer laser light (193 nm, typically 0.1–10 $mJ/cm^2$-pulse) and mercury lamps for typical total exposures of 0.01–10 $J/cm^2$ of exposed surface area. Patterns are typically generated by exposure through a lithographic mask composed of UV opaque and UV transparent regions in contact with the surface, but may also be formed using projection printing, direct laser writing, or electron beam lithography.

The crosslinking agents bearing two different reactive functional groups are known as heterobifunctional crosslinkers, and the two functional groups are reactive toward different and distinct chemical moieties, typically thiols, benzylhalides and amines. Other functional groups are known and can be useful in the method of the present invention. Functional groups reactive toward amines include but are not limited to N-succinimide esters, isothiocyanates, imidoesters and nitroaryl halides. Thiol reactive groups include but are not limited to maleimides, iodoacetyl, pyridyl disulfide, and other disulfides. A heterobifunctional crosslinker found useful for the covalent attachment of a thiol-modified synthetic DNA to an aminosilane-modified substrate was succinimidyl 4-(p-maleimidophenyl)butyrate (SMPB), which has an amino reactive succinimide ester and a thiol reactive maleimide group.

The photoresist to be coated onto the crosslinker-modified silane layer, and later patterned using UV irradiation can include numerous varieties, but must be sensitive to relatively low doses of light, and must require developers that do not remove or react with the crosslinker itself or the underlying silane or substrate. The developers and strippers used to remove the resist must also not interfere with the activity of the immobilized NAMs. A typical photoresist used in this invention is S-1400-11™ (a diazonaphthoquinone-type produced by Shipley Corp.; a positive-tone resist), with the aqueous alkaline developer MF312 CD27™ (0.27M tetramethylammonium hydroxide, produced by Shipley Corp.). An example of a negative photoresist that is useful in the present invention is the chemically amplified type, of which SAL601-ER7™ (Shipley), is an example.

The use of an overall negative-tone process, such as that shown in FIG. 2, is particularly advantageous in the formation of arrays or patterns composed of multiple, different NAMs (having differing base sequence or function). In this scheme, the use of a photoresist allows one to sequentially expose reactive areas of the crosslinker layer by irradiating the photoresist in the desired pattern(s). After fabrication of the array(s) or patterns is completed, residual photoresist may be removed, without compromising the functional performance of the NAMs.

The active agent to be attached to the modified surfaces can include numerous biomolecules, but for the present invention are chiefly nucleic acids molecules. Typically, these nucleic acid molecules are natural or synthetic oligomers of DNA or RNA which may be modified with a thiol or amino group in a specific location in the oligomer (or by incorporating a ribose sugar which may then be oxidized). Typically, these oligomers include from about 4 to about 400 bases, and more typically from about 20 to about 150 bases. Even larger nucleic acid oligomers may be created using these immobilized oligomers as primers for synthesis of amplified nucleic acids or by incorporation of modified nucleotides during the amplification process. The biomolecules to be attached by the method of the present invention may be also be labeled, for example, with fluorescent tags, enzymes, small antigens, radioactive elements chemiluminescent tags, magnetic tags, metal particles or other contrast agents. The preferred thiol-terminated DNA oligomers are easily prepared using automated solid-phase synthesis, preferably using phosphoramidite chemistry with a thiol-modifier modifier controlled pore glass support (i.e., the thiol group will be at the 3'-terminus of the molecule), but may also be prepared using a thiol-modifier phosphoramidite useful for incorporation of the thiol at the 5'-terminus of the oligomer, or by incorporation of sulfur at any number of desired positions (from 0→n, where n=the number of nucleic acid bases in the specific oligomer) within a given oligomer by using a sulfur containing oxidizer, such as tetraethyldithiouram (TETD, Applied Biosystems, Inc)

which forms phosphorothioate linkages at the selected positions within the backbone of the oligomer.

The activity of the biomolecule must be maintained after immobilization to the surface. For example, immobilized DNA or RNA probes must retain their ability to hybridize to a complementary DNA or RNA molecule in a sequence-specific manner, or to function as primers for nucleic acid amplification techniques.

The process and products of this invention can be used in many areas of the art. For example, DNA hybridization analysis to detect or identify a genetic target such as a specific nucleic acid sequence, microorganism, genetic disorder etc., using an immobilized nucleic acid probe is well known in the art. Similarly, the use of immobilized probes to perform sequence determination of a nucleic acid of undetermined sequence using sequential hybridization reactions to a large number of immobilized probes has been reported. Likewise, the use of large populations of different, non-immobilized nucleic acid molecules have been used to identify small and macromolecular ligands that are capable of sequence-specific binding with certain nucleic acid molecules. Also, nucleic acid oligomers immobilized on surfaces may be used as primers for the amplification of other nucleic acids molecules of known or unknown sequence using standard thermal cycling techniques and the addition of a second, unimmobilized appropriate primer.

In an application involving an immobilized DNA oligomer used for capture and detection of a complementary (target) DNA molecule, the complementary (target) sequence may be labeled with biotin, a fluorescent dye or radioactivity (typically $^{32}$p) using synthetic, labeled primers, or direct incorporation of the label into the molecule to be detected during an amplification step. For the types of patterned arrays described in the present invention, a significant advantage over the prior art is the capability to immobilize large numbers of identical, oligomeric nucleic acid probe molecules in a small surface area. Using the present invention, immobilized nucleic acids confined to areas of 1 μM×10 μM have been detected and resolved from adjacent nucleic acid modified areas, and nucleic acids immobilized according to the invention have been found suitable for hybridization with complementary but not with mismatched nucleic acid molecules.

The specific conditions for each of the steps described for the present invention, to obtain patterns or arrays of oligomeric NAMs that may be non-covalently or covalently bound to the surface, may vary greatly depending on the specific reagents and equipment used. The crosslinker, photoresist and NAM should be chosen such that none of these (or steps used to process or remove these) are destructive to the underlying silane film, and the assembly of steps are designed to promote maximum density of functional NAMs in a designated area on the surface. The density of functional NAMs in a designated area may be increased, for example, by using a commercially available C3–C6 spacer between thiol and the NAM, by varying the density of the organosilane film on the substrate, or by designing the immobilized NAM so it lacks ability to bind itself (i.e., not self-complementary), or by choosing a substrates with greater surface area, such as glass or fused silica.

In the preferred usage, covalent immobilization of functional nucleic acids on silicon substrates uses an amino-terminated silane, and a heterobifunctional crosslinker to bind a high density of synthetic, thiol-terminated DNA oligomer to a planar surface. It has been determined using radiolabeled thiol-modified DNA oligomers composed of 20 bases that densities of 45–75 pMoles/cm$^2$ are achieved on silicon; depending on the exact base sequence of the immobilized oligomer between 3 and 47% of the immobilized molecules are capable of selective hybridization with a complementary DNA oligomer.

Information that may assist in the practice of the present invention can be found, for example, in Eigler (sic) et al., U.S. Pat. No. 5,077,210 and Ligler et al., U.S. patent application Ser. No. 07/691,491, filed Apr. 26, 1991 and its parent application, U.S. Ser. No. 07/182,123, all of which are incorporated by reference herein in their entirety, for all purposes. Additionally, the attachment of aminosilanes to a silica substrate is further discussed in Lowe et al., U.S. Pat. No. 4,562,157, the entirety of which is incorporated herein by reference for all purposes.

Having described the invention, the following examples are given to illustrate specific applications of the invention including the best mode now known to perform the invention. These specific examples are not intended to limit the scope of the invention described in this application.

EXAMPLES

Example 1

Selective, Non-Covalent Attachment of Phosphodiester DNA Oligomers to Organosilane Surfaces Thin films of the organosilanes (SAMs) were formed on acid-cleaned fused silica slides from N-(2-aminoethyl)-3-aminopropyltrimethoxysilane (EDA), trimethoxysilylpropyldiethylenetriamine (DETA), and the fluorinated silanes 13F (tridecafluoro-1,1,2,2-tetrahydrooctyl-1-dimethylchlorosilane), and 13F-Cl$_3$(tridecafluoro-1,1,2,2-tetrahydrooctyl-1-trichlorosilane). An acid-cleaned slide was also tested. The methods used for acid cleaning and SAM preparation are described in J. M. Calvert, W. J. Dressick, C. S. Dulcey, J. H. Georger, D. A. Stenger, T. S. Koloski and G. S. Calabrese, *Polymers for microelectronics*, ACS Symposium Series, V537, edited by C. D. Wilson, L. F. Thompson, and S. Tagawa, American Chemical Society, Washington, D.C. 1993, p210; and R. L. Geer, D. A. Stenger, M. S. Chen, J. M. Calvert, R. Shashidar, Y. Jeong, and P. Pershan, submitted to Langmuir. The slides were immersed in a solution of radiolabelled (γ-32P) synthetic DNA oligomer of sequence $(GT)_{10}$, which was prepared by automated DNA synthesis using standard phosphoramidite chemistry on an Applied Biosystems Model 394 synthesizer. The trityl-on oligomer was purified (to >90% full length material) using C18 solid phase extraction columns. Radiolabeling of the 5-OH group of the oligomer was accomplished using γ-32P-ATP (DuPont NEN) and T4 polynucleotide kinase from Gibco-BRL following manufacturer's protocol. The radiolabeled synthetic DNA was separated from free radioactive γ-32P-ATP using NENSORB purification columns (DuPont-NEN), following manufacturer's directions. The purified radiolabeled DNA was diluted in high purity distilled and deionized (>18mΩ) H$_2$O to a concentration of 3 μM as determined by UV absorbance at 260 nm, and extinction coefficients calculated using Oligo 4.1 software (National Biosciences, Inc). The slides were immersed for 17 hr at room temperature, with shaking, and were then washed in three changes of fresh, high purity distilled and deionized water, and dried on filter paper. The slides were placed on autoradiographic film for 18 hrs. Following development of the film, the slides were broken, placed in liquid scintillation vials with 10 ml of Fisher brand Scintiverse IV scintillant, and counted. Quantification of the radiolabeled DNA was accomplished by determining the oligomer concentration using UV spectroscopy, as well as the number of counts per minute (CPM) for an aliquot of known volume, then converting this to a specific activity for the oligomer (CPM/pMole). The results are given in tabular form below (Table 1), and indicate that the aminosilane SAMs of EDA and DETA permit attachment of the radiolabeled DNA, while the acid-cleaned slide, the 13F and 13F-Cl$_3$ SAMs did not bind appreciable amounts of DNA. These results were supported by observation of the characteristic DNA absorbance peak at 260 nm in the UV spectra of the EDA and DETA, but not on the acid-cleaned, 13F, or 13F-Cl$_3$ treated slides.

DNA also bound to films prepared from (aminoethylaminomethyl) phenethyl-trimethoxysilane (PEDA) on fused silica (1% PEDA in 1 mM CH$_3$COOH in MeOH, 20 min at 25 C., rinse twice in MeOH, then baked at 120 C. for 5 min), as demonstrated by the presence of the characteristic DNA absorbance peak at 260 nm in the UV spectrum of these slides.

Other organosilanes to which the DNA does not appear bind as evidenced by the lack of an absorbance peak at 260 nm (DNA absorbance maxima) include acid-cleaned fused silica slides treated as follows: octadecyltrichlorosilane (1% in toluene, 5 min, 25 C.) or chloromethylphenyltrichlorosilane (1% in toluene, 10 min, 25 C.) or phenethyltrichlorosilane (1% in toluene for 6–7 min, 25 C.) or mercaptomethyldimethylethoxysilane (2% in toluene for 60 min); all were rinsed in two changes of fresh toluene, then baked on a hot plate at 120 C. for 3 min, before treatment with 1 µM synthetic DNA oligomer [5'-(CAGT)$_5$-3'] in dI water for 1 hr at room temperature. Slides were rinsed and dried as described above, then examined using UV spectroscopy. No absorbance at 260 nm was detected for any of these organosilane films, nor for acid-cleaned fused silica only.

TABLE 1

Binding of Radiolabeled Oligomer IV (3 µM) to SAMs on Fused Silica.

|  | H$^+$— cleaned slide | EDA | DETA | 13F | 13F—Cl$_3$ |
|---|---|---|---|---|---|
| CPM Bound | 5630 | 85,155 ± 7373 | 86,370 ± 19,419 | 11,417 ± 1212 | 5882 ± 518 |
| pMoles | 5.8 | 87.9 ± 7.6 | 89.1 ± 20.0 | 11.8 ± 1.3 | 6.1 ± 0.5 |
| DNA/in$^2$ |  |  |  |  |  |

Example 2

Colorimetric Detection of a Biotin-Labeled Oligomer Attached to DETA SAM

A DETA SAM was formed on acid-cleaned fused silica as described (Calvert et. al., *Polymers for Microelectronics*). A DNA oligomer of the sequence: 5'-biotin-ACTG-ACTG-ACTG-ACTG-ACTG-3' was prepared using standard phosphoramidite chemistry. The biotin group was incorporated using either a commercially available biotin-phosphoramidite (to place the biotin at the 5'terminus of the oligomer) or 1 µM biotin modifier controlled pore glass synthesis column (to place the biotin group at the 3'-terminus of the oligomer, both from Glen Research, Sterling, Va.), following the manufacturer's instructions. The labeled oligomer was purified before further use using a C18 solid phase extraction column. Aliquots (5 µl of a 1 µM solution in high purity, distilled and deionized water) of the biotin-labeled DNA oligomer of sequence (ACTG)$_5$ were placed on the surface of the DETA SAM-modified fused silica slide. At the end of 15 min, the droplets were washed away by immersion in three changes of water. The slide was then placed in 20 ml of blocking solution A [to prevent non-specific adsorption of protein; 1% purified casein, 0.1% sarkosyl, 0.02% SDS in 5× SSC (0.75M sodium citrate-sodium chloride buffer)] for 15 min at 24° C. Streptavidin-horseradish peroxidase (SA-HRP) was added to a final dilution of 1:500, and the slide incubated for 15 min at 24° C. The slide was then immersed twice in PBS-0.05% TWEEN 80 ™, and once in PBS (1–5 min each time), and finally placed in a solution containing the HRP substrate tetramethylbenzidine (TMB). TMB produces a blue colored precipitable product when it reacts with peroxidase. Blue circles corresponding to the location of the 5 µl aliquots of DNA solution placed on the fused silica slide were observed following this treatment. The surrounding areas on the fused silica slide remained transparent and did not turn blue, indicating that the biotin-labeled DNA oligomer was confined to regions on the DETA SAM-modified slide where the aliquots were originally placed, and that no non-specific binding of the SA-HRP to these other areas of the slide occurred. Had non-specific binding of the SA-HRP occurred on the slide, areas of the slide not treated with the biotin-labeled DNA oligomer would have also turned blue.

Example 3

Selective Hybridization of a DNA Oligomer Attached by Electrostatic Binding to an Aminosilane Film on Fused Silica Slides Small aliquots (5 µl of 1 µM solution in water) of a DNA oligomer of sequence 5'-(ACTG)$_5$-3' (I) were placed on DETA SAMs on fused silica slides (prepared as described in Example 1), then rinsed off in two changes of PBS-0.05% Tween, and one time in PBS (5 min per treatment). The slides were placed in blocking buffer A (see Example 2) for 15 min, then two slides were immersed in a 1 µM solution of a complementary oligomer [II, 5'-(CAGT)$_5$-3'] and two were placed in a 1 µM solution of a mismatched oligomer [III, 5'-(CAAT)$_5$-3'] , for 1 hr at room temperature. The slides were rinsed briefly in two changes of 2× SSC (0.3M sodium citrate-sodium chloride buffer, pH 7.0), then 1 slide of each pair was placed in 0.1× SSC (0.015M sodium citrate-sodium chloride, pH 7.0) at 23° C., and the other slide in 0.1× SSC at 30° C. [The annealing temperature of the perfectly matched I/II pair is estimated at 32° C. in 0.1× SSC using algorithms employed by Oligo 4.1 software]. The slides were left for 15 minutes, then all slides were exposed to 1:500 dilution of streptavidin-horseradish peroxidase in blocking buffer A for 15 min at room temperature. The slides were rinsed twice in PBS, then placed in a solution of the HRP substrate, TMB. (see example 2, above). Blue circles were observed on the slides on which aliquots of oligomer I had been placed, then treated with the complementary, biotin-labeled oligomer II, however, no reaction was seen with the mismatched I/III pair. These results indicate that a DNA oligomer immobilized via electrostatic means on an organosilane SAM is able to form duplexes selectively with its complementary partner, but will reject hybridization with a mismatched oligomer.

Example 4

Demonstration of Electrostatic Binding of DNA Oligomer to Aminosilane Film on Fused Silica DETA SAMs were formed on fused silica slides as described in Example 1. Slides were immersed in 1 µM water solution of DNA oligomer 5'-(ACTG)$_5$-3' for 1 hr at 25 C., then rinsed in 3 changes of dI water. UV spectra were taken of the dried slides. Duplicate slides were then placed in solutions containing: high purity dI water only; 50 mM Na-phosphate, pH 7.6; 50 mM Na-phosphate, 250 mM NaCl, pH 7.6; or 50 mM Na-phosphate, 1M NaCl pH 7.6 for 1, 2, 4 and 21 hr at 25 C. The UV absorbance at 260 nm (DNA maxima) was compared for all slides. At high salt (50 mM Na-phosphate, pH 7.6 with either 250 mM NaCl or 1M NaCl, after 2 hrs 80% of the DNA has desorbed from the DETA surface. For 50 mM Na-phosphate, 1M NaCl pH 7.6, after 21 hr, less than 10% of the adsorbed DNA remains. These results indicate that electrostatic interactions between the negatively charged phosphate groups of DNA and positively charged amino groups of the aminosilane SAMs are responsible for DNA deposition from solution onto these SAMs.

Example 5

Selective, Electrostatic Binding of Double Stranded Herring Sperm DNA on Aminosilane Films on Fused Silica Slides Acid cleaned and DETA-treated fused silica slides were treated with a 100 µg/ml solution of herring sperm DNA in water for 30 min at 25 C. Slides were rinsed 3× in dI water and dried under a stream of filtered $N_2$. UV spectra were taken of the slides before and after treatment. Acid cleaned slides did not bind double-stranded DNA, while the DETA SAM modified slides showed the characteristic DNA absorbance peak at 260 nm ($A_{260}$=0.0071, vs -0.0004 for acid-cleaned slide).

Example 6

Non-Covalent Binding of P(S) DNA on/ Aminosilane Films on Fused Silica Slides

Figure 6:
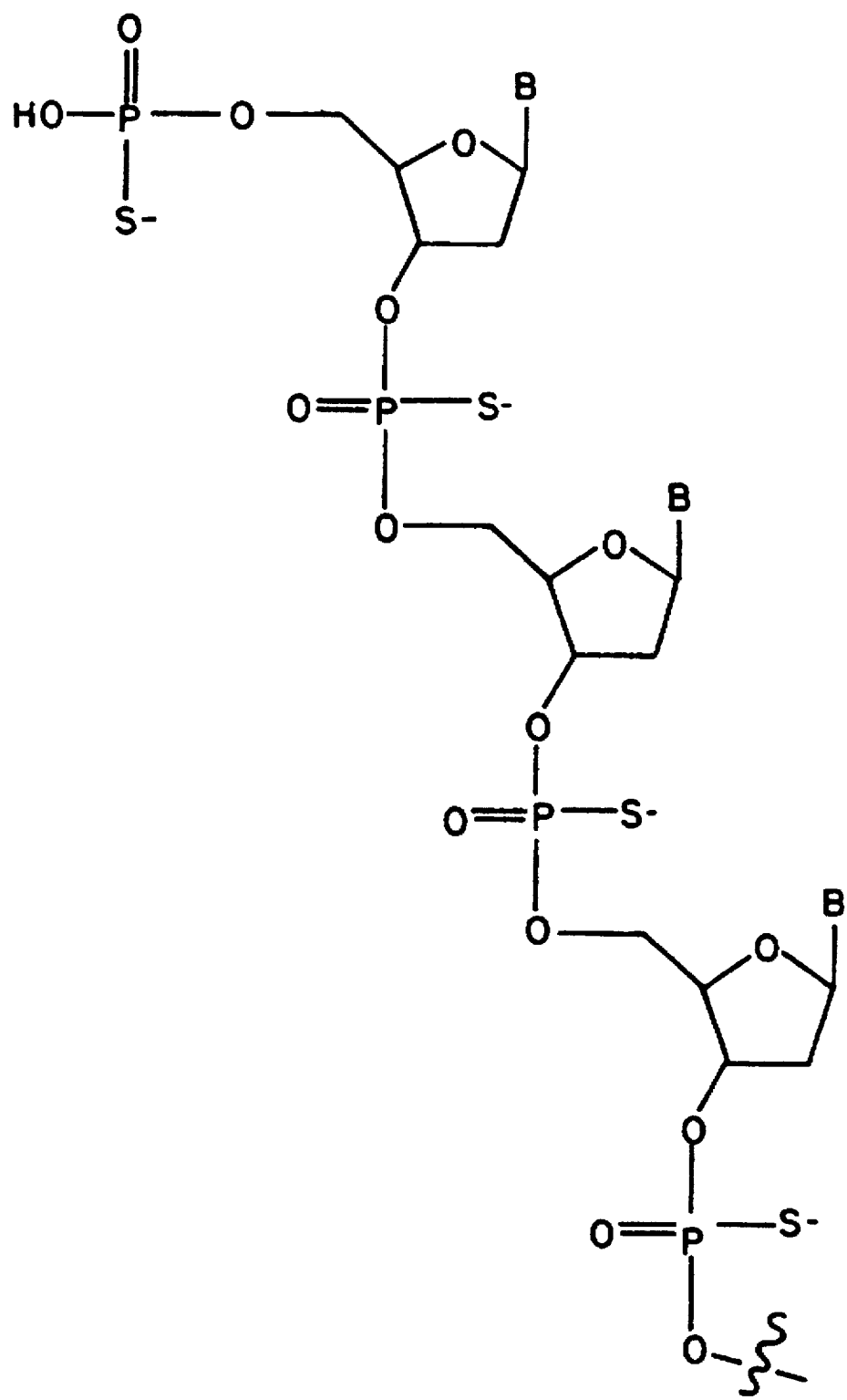
FIG. 6 shows the structure of the phosphorothioate DNA backbone.

The phosphorothioate oligomer [P(S)], a congener of the native phosphodiester DNA molecule in which the negatively charged internucleotidic phosphate oxygen is replaced by a negatively charged sulfur atom, is prepared using standard phosphoramidite chemistry on the automated DNA synthesizer using a commercially available thiolating/oxidizing reagent, tetraethylthiouram (TETD) instead of the customary $I_2$-based oxidizer. Purification and quantification of the product DNA oligomer are performed as in Examples 1 and 2. The structure of the phosphorothioate DNA congener is given in FIG. 6.

Fused silica slides were treated with PEDA (as described in Example 1), then immersed in a 1 µM solution of phosphorothioate DNA oligomer [5'-(ACTG)$_5$-3', P(S)] in dI water for 1 hr at 25 C. The slides were rinsed 3 times in dI water, dried under filtered $N_2$, then examined using UV spectroscopy. The slides which were treated with the P(S) oligomer yielded the characteristic DNA absorbance peak at 260 nm, while the untreated slide did not display this peak.

Example 7

Photochemical Modification of a PEDA Film to Form DNA Patterns

PEDA films were prepared on fused silica slides as described in Example 1. Advancing contact angle measurements determined using 5–10 µl water droplets on a Zisman-type goniometer yielded values of 60±2 degrees.

Following formation of PEDA SAM on fused silica, a slide was clamped to a chrome-on-quartz lithographic mask and exposed to monochromatic 193 nm deep UV laser pulses using a Questek Ar—F excimer laser. Total exposures of 350 mJ/cm$^2$ (0.3 mJ/pulse) were employed. The smallest features on the mask employed were 100 µM ×100 µM pads. PEDA slides patterned in this way were subsequently immersed in a 1 µM solution of biotinylated oligomer 5'-(ACTG)$_5$-3' for 30 min at room temperature, then the slide was blocked for 15 min and labeled DNA detected using SA-HRP as described in Example 2, above. Pattern features were successfully observed using bright-field and differential contrast microscopy at 50× magnification.

Example 8

Patterned Non-Covalent Immobilization of Synthetic DNA on Negative Photoresist-Coated Aminosilane Films on Fused Silica Slides Fused silica slides were treated with DETA as described above (Example 1) to form films. DETA slides were then spin-coated with negative photoresist SAL601-ER7™ (Shipley) for 30 seconds at 7K rpm, then baked at 90 C. for 30 min. A lithographic mask was placed on top of the photoresist-treated slide, then the assembly was exposed to a 254 nm UV lamp for 3 seconds (17.4 mJ, 5.8 mW/cm$^2$). The slide was developed by baking at 115 C. for 5 min, then treatment in MF312 CD27 developer for 6 minutes. The slides were rinsed with dI water, and dried under filtered $N_2$. A 1 µM solution of 5'-biotin-(ACTG)$_5$-3' in dI water was pipetted onto the exposed and developed surface of the DETA/SAL601-E17™-treated slide, and allowed to sit for 15 min at 25° C. The slide was rinsed in three changes of dI water, then immersed in blocking buffer A (see Example 2, above) for 15 min at 25° C. The slide was rinsed three times in 0.1M Tris-0.015M NaCl, pH 7.5, then treated with 1:500 dilution of SA-HRP (see Example 2) in blocking buffer A for 15 min at 25° C. After rinsing slides three times in 0.1M Tris-0.015M NaCl, pH 7.5, they were immersed in the HRP substrate TMB, whereupon blue color appeared on the slide as a negative tone image (blue appears where the chrome regions on mask protected the underlying photoresist/DETA; regions which were irradiated are not removed by the developer). Differential interference contrast microscopy was used to visualize the smallest feature sizes (100 µM$^2$ pads).

Example 9

Covalent Immobilization Using Aminosilane Films Modified with a Heterobifunctional Crosslinker, and Thiol-Modified DNA Oligomers Thiol-modified DNA oligomers were prepared using standard phosphoramidite chemistry and an automated DNA synthesizer with the following substitutions: a commercially available, 1 µM 3'-thiol C3 S—S modifier DNA synthesis column (Glen Research) was used instead of the usual DNA base (A, C, T or G) synthesis column, and a 0.02M $I_2$ oxidizer was used instead of the usual 0.1M $I_2$ oxidizer. Purification and quantification of the product DNA oligomer was performed as described in Examples 1 and 2. A concentrated solution of the protected disulfide form of the oligomer [5'-(ACTG)$_5$-S-S-3'] was prepared in water, then treated with a solution of dithiothreitol (DTT) in phosphate buffer (final concentrations: 30 nMoles DNA oligomer 0.04M DTT, 0.17M Na-phosphate, pH 8.0) for 15–20 hr at 25 C. to reduce the disulfide oligomer to its free thiol form [5'-(ACTG)$_5$-SH-3'] . Immediately before addition to SMPB crosslinker-modified DETA or EDA substrates (see below), extraction of the solution (typically 1 ml volume) with 3 equivalent portions of ethyl acetate (to remove excess DTT), is performed to yield the free thiol form of the oligomer. This form of the oligomer will be referred to as 5'-Biotin-(ACTG)$_5$-SH-3' henceforth.

EDA and DETA films were prepared on fused silica slides as described in Example 1. A 1 mM solution of the heterobifunctional crosslinker SMPB {succinimidyl 4-(p-maleimidophenyl)butyrate} was prepared by dissolution in 100 µl DMSO, then mixture with 30 ml of 20% DMSO, 80% MeOH. EDA or DETA slides were treated with the SMPB solution in glass jars for 2 hr at 25° C. Slides were rinsed three times in fresh MeOH, and dried under a stream of filtered N$_2$. Slides were then transferred to a fresh glass jar along with 30 ml degassed buffer (10 mM HEPES, 5 mM EDTA, pH 6.6) to which approximately 30 nMoles of the free thiol form of the DNA oligomer has been added, then placed into a Ar-purged glovebag. The reaction is conducted under a positive pressure of Ar (to avoid oxidation of the thiol-modified DNA oligomer) for 2 hr at 25 C., then slides are rinsed once in fresh HEPES buffer and twice in dI water, the dried under a stream of filtered N$_2$.

To remove non-covalently bound DNA from the slides, slides were treated for 24 hr with 50 mM Na-phosphate, 1M NaCl, pH 7.6 at 25 C., then rinsed three times with dI water, and dried under N$_2$ (see Example 4).

Reactions were followed by UV spectroscopy, after each succeeding layer was deposited on the slide: DETA or EDA, then SMPB, then total DNA, then covalently bound DNA remaining after treatment under high salt concentrations to remove any electrostatically-bound DNA. EDA and DETA films show no absorbance above 210 nm; the SMPB film shows a small absorbance at approximately 220 nm (due to the phenyl group), while the total DNA peak is clearly observed at 260 nm, and is reduced by approximately 30% following treatment under high salt conditions.

Example 10

Covalently Bound DNA Patterns Fabricated Using 193 nm Irradiation of Aminosilane Films on Fused Silica or Glass Slides PEDA films were prepared on fused silica or glass microscope slides, as described in Example 5. The films were irradiated with pulsed 193 nm ArF laser irradiation (405 mJ/cm$^2$, 0.81 mJ/pulse) through a chrome-on-glass mask, then rinsed briefly in 1M NaCl. The slides were treated with a 1 mM solution of SMPB in DMSO-Ethanol (20:80), and the 5'-biotin-ACTG)$_5$-SH-3' DNA as described in Example 9 for EDA and DETA films. The slides were treated with 50 mM Na-phosphate, 1M NaCl, pH 7.6 for 24 hr to remove electrostatically (non-specifically) bound DNA, then were blocked using Buffer A. The biotin-labeled DNA was visualized using an enzyme-linked colorimetric assay as described in Example 5. Patterns were visible using either brightfield or differential interference contrast (DIC) microscopy at 50× magnification.

Example 11

Covalently Bound DNA Patterns Fabricated Using 193 nm Irradiation of Aminosilane/Crosslinker Films on Fused Silica or Glass Slides PEDA films were prepared on fused silica or glass microscope slides, as described in Example 5. The films were then treated with a 1 mM solution of SMPB in DMSO-Ethanol (20:80) as described above in Example 9. The films were irradiated with pulsed 193 nm ArF laser irradiation (405 mJ/cm$^2$, 0.81 m J/pulse) through a chrome-on-glass mask, then rinsed briefly in 1M NaCl. Following this rinse, the slides were treated with deprotected 5'-biotin-(ACTG)$_5$-SH-3' DNA as described in Example 9 for EDA and DETA films. The slides were treated with 50 mM Na-phosphate, 1M Nacl, pH 7.6 for 24 hr to remove electrostatically (non-specifically) bound DNA, then were blocked using Buffer A. The biotin-labeled DNA was visualized using a enzyme-linked colorimetric assay as described in Example 5. Patterns were visible using either brightfield or differential interference contrast (DIC) microscopy at 50× magnification.

Example 12

DNA Patterns Fabricated Using UV Lamp Irradiation of Positive photoresist-Coated Aminosilane Films on Fused Silica Substrates DETA films were prepared on fused silica slides as described in Example 1, then treated with a 1 mM SMPB solution as described in Example 9. S-1400-11 positive-tone photoresist (Shipley Corp.) was spin-coated onto the DETA/SMPB surfaces (5K rpm) and then baked at 90 C. for 30 min. Slides were exposed through a chrome-on glass mask using a 254 nm UV lamp (40–50 mJ/cm$^2$ total exposure, 8–10 sec), then developed using MF312 CD27198 developer (Shipley Corp) for 50 sec. With the positive tone resist, features that are not protected by the chrome areas of the mask dissolve away upon development, exposing the underlying silane/crosslinker layers. The slides are treated under an Ar atmosphere with a 1 µM solution of deprotected 5'-biotin-(ACTG)$_5$-SH-3'DNA oligomers as described in Example 9, then slides are rinsed with fresh HEPES buffer and dI water and dried under N$_2$. Visualization of DNA patterns using the colorimetric method described in Example 5 was accomplished without further treatment of the slides. Patterns were also visible using the colorimetric detection scheme following treatment of the slides for 24 hr in 50 mM Na-phosphate, 1M NaCl to remove electrostatically (i.e., non-specifically) bound DNA from the surface.

Example 13

Demonstration of Retention of Covalently Immobilized DNA on Aminosilane-Crosslinker Surfaces Following Treatment with Photoresist Developer MF312 CD27

DETA films were prepared on fused silica slides (see Example 1), and treated with the SMPB crosslinker as described in Example 9. Slides were then treated with: 1) MF312 CD27 developer (50 sec) followed by the deprotected 5'-Biotin-(ACTG)$_5$SH-3' DNA oligomer (see Example 9), or 2) the deprotected 5'-Biotin-(ACTG)$_5$-SH-3' DNA oligomer (see Example 9), then the MF312 CD27 developer for 50 sec. In each case, DNA was visualized following detection using colorimetric methods described in Example 5. These results suggest that both the aminosilane-crosslinker linkage and the crosslinker-DNA-biotin linkages may be stable to the harsh developing (pH>13) conditions require for the photoresist.

Obviously, many modifications and variations of the present invention are possible in light of the above teachings. For example, although the present specification has described the invention with particular reference to organosilanes as examples of nucleic acid-binding coating molecules, it should be understood that other molecules may be used for the nucleic acid-binding substrate coating. That is, any coating molecules having one functional group that reacts with the surface and another transformable functional group that does not bind to the surface or other coating molecules, but whose ability to directly or indirectly bind nucleic acid molecules is reversed by irradiation (i.e., irradiation destroys or creates the ability to covalently or non-covalently bind, either directly or indirectly, nucleic acid molecules), may be used for the substrate coating in place of the nucleic acid-binding organosilane molecules. It is therefore to be understood that, within the scope of the appended claims, the invention may be practiced otherwise than as specifically described.

What is claimed is:

1. A method of attaching pre-formed hybridizable synthetic nucleic acid oligomers, modified to include a thiol group, to selected portions along a surface of a substrate to form a pattern of synthetic hybridizable nucleic acid oligomers thereon, comprising the steps of:

covalently binding an organosilane coating to said surface of said substrate, the organosilane molecules of said covalently-bound organosilane coating having, at a site distal from a site of attachment of said organosilane molecule to said surface, at least one active site incapable of binding to said surface and incapable of binding to the other organosilane molecules of said organosilane coating, but available as a covalent attachment site for binding to a heterobifunctional crosslinker, said heterobifunctional crosslinker including a first reactive site that covalently binds to said at least one active site of said organosilane molecule of said coating, a second reactive site available for directly covalently binding to said thiol group of said preformed synthetic hybridizable nucleic acid oligomers, thus forming an organosilane-coated assembly;

reacting said organosilane coating with said heterobifunctional crosslinker;

defining, after said reacting step, a pattern within said organosilane coating including a first region, said first region including said organosilane molecules, and said organosilane molecules in said first region retaining said at least one active site available for binding said heterobifunctional crosslinker, and a second region that lacks organosilane molecules having an available active site for binding said heterobifunctional crosslinker, by exposing said organosilane-coated assembly to a pattern of radiation thereby forming a patterned surface;

exposing said patterned surface to said modified preformed synthetic nucleic acid oligomers to selectively and covalently attach said thiol group of said modified pre-formed synthetic nucleic acid oligomers to said first region and to non-specifically adsorb said modified pre-formed synthetic nucleic acid oligomers to said patterned surface;

removing said non-specifically adsorbed pre-formed synthetic nucleic acid oligomers from said patterned surface, thereby forming a pattern of covalently attached hybridizable synthetic nucleic acid oligomers upon said substrate.

2. The method of claim 1, wherein said radiation is ultraviolet radiation.

3. The method of claim 2, wherein said organosilane is an aminosilane.

4. The method of claim 2, wherein said organosilane is an aminosilane and said at least one active site is a terminal amino group.

5. The method of claim 4, wherein said terminal amino group is a primary amino group.

6. The method of claim 4, wherein said aminosilane is an amino-terminated aminosilane also having a hydroxyl-reactive terminus selected from the group consisting of a trichloro group, a trialkoxy group, a dichloro group, a monochloro group, a dialkoxy group and a monoalkoxy group.

7. The method of claim 6, wherein said aminosilane is selected from the group consisting of N-(2-aminoethyl)-3-aminopropyltrimethoxysilane, trimethoxysilylpropyldiethylenetriamine, and (aminoethylaminomethyl)-phenyethyltrimethoxysilane.

8. The method of claim 1, wherein said organosilane-coated assembly is exposed to said patterned radiation by employing ultraviolet light and a lithographic mask.

9. The method of claim 1, wherein said first reactive site of said heterobifunctional crosslinker is an N-succinimide ester group, an isothiocyanate group, an imidoester group, or a nitroaryl halide group, and said second reactive site is a maleimide group, an iodoacetyl group, or a disulfide group.

10. The method of claim 12, wherein said heterobifunctional crosslinker is succinimidyl 4-(p-maleimidophenyl) butyrate.

11. The method of claim 1, further comprising the step of coating said heterobifunctional crosslinker-bound organosilane layer with a photoresist material before said step of defining said pattern, so that said second reactive sites of said underlying heterobifunctional crosslinker are rendered unavailable for covalently bonding with nucleic acid molecule.

12. The method of claim 11, wherein said step of defining said pattern includes the steps of:

exposing part of said photoresist to said pattern of ultraviolet radiation, thus forming a corresponding pattern including an exposed region of said photoresist and an unexposed region of said photoresist;

selectively removing said exposed or said unexposed region of said photoresist to expose said heterobifunctional crosslinker-bound organosilane layer underlying said selectively removed region of said photoresist, so that said second reactive sites of said heterobifunctional crosslinkers underlying said removed region of said photoresist are made available for covalently bonding with nucleic acid molecules.

13. The method of claim 1, wherein said nucleic acid oligomers have from 4 to about 400 bases.

14. The method of claim 13, wherein said nucleic acid oligomers have from about 20 to about 100 bases.

15. A method of attaching pre-formed, hybridizable, synthetic nucleic acid oligomers to selected portions along a surface of a substrate to form a pattern of hybridizable nucleic acid oligomers thereon, comprising the steps of:

covalently binding a coating of non-DNA-binding organosilane molecules to said surface of said substrate, thus forming an organosilane-coated assembly;

defining a pattern including a first region, said first region including said non-DNA-binding organosilane molecules, and a second region in which said non-DNA-binding organosilane molecules have been removed from the surface by exposing said organosilane-coated assembly to a pattern of ultraviolet radiation, thereby forming a patterned surface;

covalently binding nucleic acid-binding organosilane molecules to said patterned surface at said second region, said nucleic acid-binding organosilane molecules having, at a site distal from a site of attachment of said nucleic acid-binding organosilane molecule to said surface of said second region, at least one active site incapable of binding to said surface, incapable of binding to the non-DNA-binding organosilane molecules of said coating, and incapable of binding to said nucleic acid-binding organosilanes, but available as an attachment site for binding a heterobifunctional crosslinker, said heterobifunctional crosslinker including a first reactive site that covalently binds to said at least one active site of said organosilane molecule of said coating, and a second reactive site available for directly and covalently binding to said thiol group of said modified synthetic nucleic acid molecules;

reacting said organosilane coating with said heterobifunctional crosslinker;

exposing, after said reacting step, said patterned surface having said nucleic acid-binding organosilanes therein to said modified pre-formed synthetic nucleic acid oligomers to selectively and covalently attach said thiol group of said pre-formed, synthetic nucleic acid oligomers to said second region and to non-specifically adsorb said modified pre-formed nucleic acid oligomers to said patterned surface; and removing said non-specifically adsorbed pre-formed synthetic nucleic acid oligomers from said patterned surface, thereby forming a pattern of covalently attached hybridizable synthetic nucleic acid oligomers upon said substrate.

16. The method of claim 15, wherein said organosilane is an aminosilane and said at least one of active site is a terminal amino group.

17. A method of attaching pre-formed synthetic hybridizable nucleic acid oligomers, modified to include a thiol group, to selected portions along a surface of a substrate to form a pattern of said modified hybridizable synthetic nucleic acid oligomers thereon, comprising the steps covalently binding an organosilane coating to said surface of said substrate, the molecules of said covalently-bound organosilane coating having, at a site distal from a site of attachment of said coating molecule to said surface, at least one active site incapable of binding to said surface and incapable of binding to the other molecules of said coating, the ability of which to covalently bind a heterobifunctional crosslinker is reversed by exposure to irradiation, thus forming an organosilane-coated assembly;

defining a pattern in said organosilane coating, said pattern including a first region, said first region including said coating molecules, and said at least one active site of said coating molecules in said first region having the ability to bind said heterobifunctional crosslinker, and a second region that lacks coating molecules with the ability to bind said heterobifunctional crosslinker, by exposing said coated assembly to a pattern of radiation thereby forming a patterned surface;

reacting said organosilane coating with said heterobifunctional crosslinker, said heterobifunctional crosslinker including a first reactive site that covalently binds to said at least one active site of said coating molecules in said first region, and a second reactive site available for directly and covalently binding to said thiol group of said modified synthetic nucleic acid oligomers;

exposing said patterned surface having said nucleic acid-binding organosilanes therein to said modified pre-formed synthetic nucleic acid oligomers to selectively and covalently bind said thiol group of said modified synthetic nucleic acid oligomers to said first region and to non-specifically adsorb said modified preformed synthetic nucleic acid oligomers to said patterned surface; and removing said non-specifically adsorbed pre-formed synthetic nucleic acid oligomers from said patterned surface, thereby forming a pattern of covalently attached hybridizable synthetic nucleic acid oligomers upon said substrate.

18. The method of claim 1, wherein said non-specifically adsorbed pre-formed nucleic acid oligomers are removed from said patterned surface by exposing said patterned surface to a salt of sufficiently high concentration to desorb said non-specifically adsorbed pre-formed nucleic acid oligomers from said patterned surface.

* * * * *